(12) United States Patent
Lo

(10) Patent No.: US 8,580,722 B2
(45) Date of Patent: Nov. 12, 2013

(54) PORTABLE CLEANING ARTICLE AND THE FORMING METHOD THEREOF

(75) Inventor: Yun-Chun Lo, Pingzhen (TW)

(73) Assignee: Yun-Chun Lo, Taoyuan County (TW)

( * ) Notice: Subject to any disclaimer, the term of this patent is extended or adjusted under 35 U.S.C. 154(b) by 363 days.

(21) Appl. No.: 12/820,665

(22) Filed: Jun. 22, 2010

(65) Prior Publication Data

US 2010/0323947 A1 Dec. 23, 2010

(30) Foreign Application Priority Data

Jun. 23, 2009 (TW) .................. 98120940 A

(51) Int. Cl.
*A61K 8/00* (2006.01)

(52) U.S. Cl.
USPC ............................ 510/130; 510/141; 510/447

(58) Field of Classification Search
None
See application file for complete search history.

(56) References Cited

U.S. PATENT DOCUMENTS

| | | | |
|---|---|---|---|
| 2007/0072780 A1* | 3/2007 | Reddy et al. | 510/130 |
| 2008/0214428 A1* | 9/2008 | Orlich et al. | 510/405 |

* cited by examiner

*Primary Examiner* — Necholus Ogden, Jr.
(74) *Attorney, Agent, or Firm* — Ming Chow; Sinorica, LLC

(57) ABSTRACT

A portable cleaning article includes a coated capsule and cleaning agent, in which the cleaning agent is contained within the coated capsule, the characteristic in that: the coated capsule having a thin-film layer and an oil layer that is coated over the surface of the thin-film layer to form a portable cleaning article. When the coated capsule is brought into contact with water by the user, the coated capsule dissolves in water for the cleaning agent to exert its cleaning function.

6 Claims, 5 Drawing Sheets

PORTABLE CLEANING ARTICLE AND THE FORMING METHOD THEREOF

BACKGROUND OF THE INVENTION

1. Field of the Invention

The present invention mainly discloses a cleaning article, and more particularly, a portable cleaning article in the form of water dissoluble coated capsule.

2. Description of the Prior Art

Common cleaning products in the market are usually packed is in bottles or jars, most of which are often discarded after usage instead of being recycled. This not only leads to more burden of waste disposal but also results in problems regarding environmental protection.

A trouble that generally accompanies outdoor travels is the need to bring along cleaning articles including hair shampoo, body shampoo, facial cleanser, and/or makeup remover that is frequently needed by females. However, most of these cleaning articles are sold in bottles or jars. Although products in travel size containers are available for purchase at present, yet the amount of items of cleaning articles often exceeds what is needed during the travels, and the containers also add to the weight of luggage, especially in the transportation process, which thus leads to inconvenience when traveling. Moreover, disposal of these containers after usage results in more pollution for the environment. Therefore, to solve the problems as described above, the present invention discloses a water-dissoluble, non-polluting, portable cleaning article that is at the same practical and environmental-friendly.

SUMMARY OF THE INVENTION

In consideration of the above, one primary objective of the present invention is to provide a portable coated capsule that helps reduce the volume of cleaning article brought along and is convenient for the user during outdoor travels or business trips.

Another objective of the present invention is to provide a water-dissoluble, environmental-friendly, portable cleaning article that dissolves in water and exerts cleaning function when being brought into contact with water.

According to the aforementioned objectives, the present invention provides a portable cleaning article comprising coated capsule and cleaning agent, in which the cleaning agent is contained within the coated capsule, the characteristic in that: the coated capsule includes a thin-film layer and an oil layers that is coated on the surface of the thin-film layer, through the design of which the oil layer is able to isolate external water vapor to prevent the thin-film layer from reacting with the water vapor, wherein when the coated capsule is brought into contact with water, the coated capsule dissolves in water and the cleaning agent contained within can exert its cleaning function.

The present invention further provides a portable cleaning article comprising coated capsule and cleaning agent, wherein the cleaning agent is contained within the coated capsule, the to characteristic of which lies in that: the coated capsule includes a first thin-film layer for containing the cleaning agent and a second thin-film layer for coating the first thin-film layer containing the cleaning agent to form the coated capsule, wherein when the coated capsule is brought into contact with water, the coated capsule dissolves in water and the cleaning agent contained within can exert its cleaning function.

Furthermore, the present invention discloses a method for forming portable cleaning article, comprising: providing a first plate, on which is a first opening; placing a first thin-film layer on the first plate and covering the first opening; vacuum pumping for the first thin-film layer on the first plate covering the first opening to form a hemispherical structure; heating the first plate to soften the first thin-film layer on the first plate; providing a second plate, on which is a second opening; placing a second thin-film layer on the second plate and covering the second opening; heating the second plate to soften the second thin-film layer on the second plate; filling the hemispherical structure of the first plate with cleaning agent of certain volume; joining the second plate with the first plate for the first thin-film layer on the first plate and the second thin-film layer on the second plate to assemble to form a first capsule structure and for the cleaning agent to be contained in the first capsule; repeating the aforementioned steps for a third thin-film layer to form on a third plate and a fourth thin-film layer to form on a fourth plate, wherein the third thin-film layer or the fourth thin-film layer is a hemispherical structure; and joining the to third plate with the fourth plate for the first capsule to be placed in the hemispherical structure on the third plate or the fourth plate and for the third thin-film layer on the third plate and the fourth thin-film layer on the fourth plate to be closely joined and coat the first capsule to form portable cleaning article.

DESCRIPTION OF THE PREFERRED EMBODIMENT

The present invention mainly provides a portable cleaning article and the forming method thereof. In order to thoroughly understand the present invention, the portable cleaning article and its forming method will be described in detail in the following. Apparently, the embodiment of specific details of the present invention familiar to those who are skilled in the art related to the cleaning article is not limited in the present invention. Yet preferred embodiments of the present invention will still be described in detail as below. In addition to what is described in detail, the present invention can also be extensively applied in many other embodiments without limited scope. Various modifications and similar arrangements can thus be made without departing from the spirit and scope of the present invention. Therefore, the scope of the present invention is defined only by the appended claims, which should be accorded the broadest interpretation so as to encompass all such modifications and arrangements.

Figure 1A:
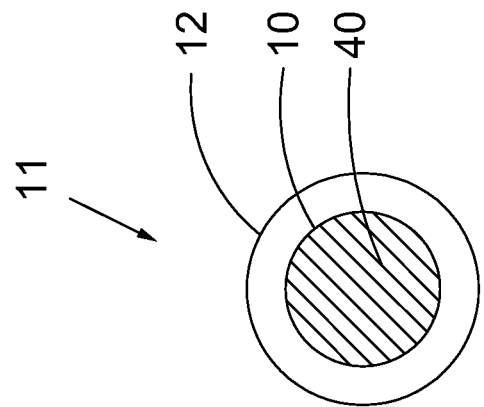
FIG. 1A is a schematic view of the coated capsule according to the art disclosed by the present invention.
Figure 1B:
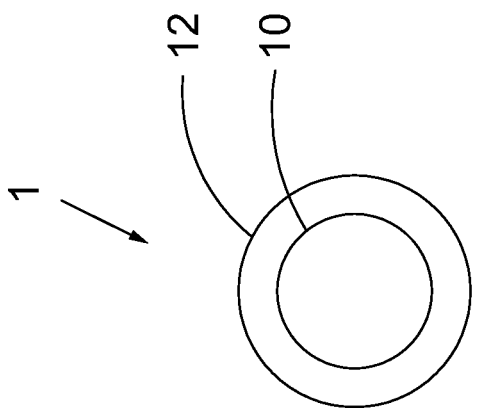
FIG. 1B is a schematic view of the portable cleaning article according to the art disclosed by the present invention.

Referring to FIG. 1A, which is a schematic view of coated to capsule disclosed by the present invention. In FIG. 1A, a coated capsule 1 includes a thin-film layer 10 and an oil layer 12, wherein the oil layer 12 is coated over the whole surface of the thin-film layer 10. In the present embodiment, the material of the thin-film layer 10 can be PVA (polyvinyl alcohol) and the molecular weight (Mw) of the thin-film layer 10 is about 1,000~10,000. Then, referring to FIG. 1B, which is a schematic view of portable cleaning article disclosed by the present invention. In FIG. 1B, the portable cleaning article 11 includes the thin-film layer 10, the oil layer 12, and liquid of certain volume 40, in which the liquid of certain volume 40 is contained in the coated capsule formed by the thin-film layer 10. Similarly, an oil layer 12 is coated on the surface of the thin-film layer 10 for isolating the thin-film layer 10 from water vapor in the external surroundings to prevent the thin-film layer 10 from dissolving and breaking. Since the portable cleaning article 11 may be placed in air for long time, the thin-film layer 10 may react with water vapor contained in air and dissolve and break, which thus leads to leakage of the cleaning agent 40 due to breaking of the thin-film layer 10 and loss of preservation effect of the coated capsule 1. Here the material for forming the thin-film layer 10 can also be polyols such as sorbitol to increase the stability of the thin-film layer 10. In addition, the liquid of certain volume 40 can be a cleaning agent, water-based or oil-based, and the cleaning agent can also be a surface-active agent such as ionic surface-active agent, non-ionic surface-active agent, or amphoteric surface-active agent. In the present embodiment, the liquid of certain volume 40 can be facial cleanser, body shampoo, or any kind of lotion used to protect or moisturize the skin.

Figure 2A:
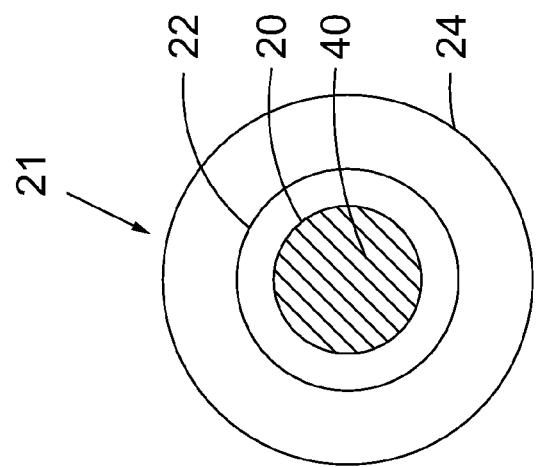
FIG. 2A is a schematic view of another preferred embodiment of the coated capsule according to the art disclosed by the present invention.

Then, referring to FIG. 2A, which is a schematic view of another preferred embodiment of coated capsule disclosed by the present invention. In FIG. 2A, the coated capsule 2 includes: a first thin-film layer 20, an oil layer 22, and a second thin-film layer 24, wherein the oil layer 22 is coated on the surface of the first thin-film layer 20, which is then coated by the second thin-film layer 24 to form coated capsule 2. In the present embodiment, the material of the first thin-film layer 20 and the second thin-film layer 24 can be PVA (polyvinyl alcohol). The molecular weight (Mw) of the first thin-film layer 20 is higher than that of the second thin-film layer 24, wherein the molecular weight (Mw) of the first thin-film layer 20 is about 4000-40000 and the molecular weight (Mw) of the second thin-film layer 24 is about 1,000~10,000. However, in the most preferred embodiment of the present invention, the molecular weight (Mw) of the first thin-film layer 20 and the molecular weight (Mw) of the second thin-film layer 24 are the same, about 1,000~10,000. Moreover, in the present embodiment, since there is an oil layer 22 between the first thin-film layer 20 and the second thin-film layer 24, the oil layer 22 is able to protect the second thin-film layer 24 when the first thin-film layer 20 is in contact with external water vapor and dissolves (or melts).

Figure 2B:
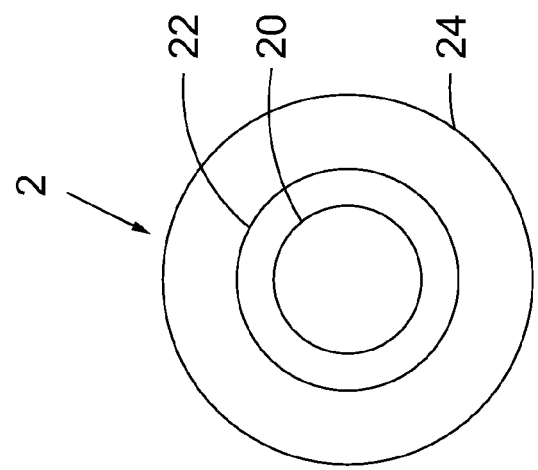
FIG. 2B is a schematic view of another preferred embodiment of the portable cleaning article according to the art disclosed by the present invention.

Then, referring to FIG. 2B, which is a schematic view of another embodiment of portable cleaning article disclosed by the present invention. In FIG. 2B, the portable cleaning article 21 includes: a first thin-film layer 20, an oil layer 22, a second thin-film layer 24, and liquid of certain volume 40, wherein liquid to of certain volume 40 is contained within the first thin-film layer 20 and the surface of the first thin-film layer 20 is coated with the oil layer 22, the purpose of which is to isolate the first thin-film layer 20 from water vapor in external surroundings to prevent the first thin-film layer 20 from reacting with the water vapor and dissolve and break. The first thin-film layer 20 coated with oil layer 22 is then coated by the second thin-film layer 24 to form portable cleaning article 21. Here, the material of the first thin-film layer 20 and the second thin-film layer 24 can be polyols such as sorbitol to increase the stability of the first thin-film layer 20 and of the second thin-film layer 24. In addition, the liquid of certain volume 40 can be a cleaning agent, water-based or oil-based, and the cleaning agent can also be a surface-active agent such as ionic surface-active agent, non-ionic surface-active agent, or amphoteric surface-active agent. In the preferred embodiment of the present invention, the liquid of certain volume 40 can be facial cleanser, body shampoo, or any kind of lotion used to protect or moisturize the skin.

Figure 3B:
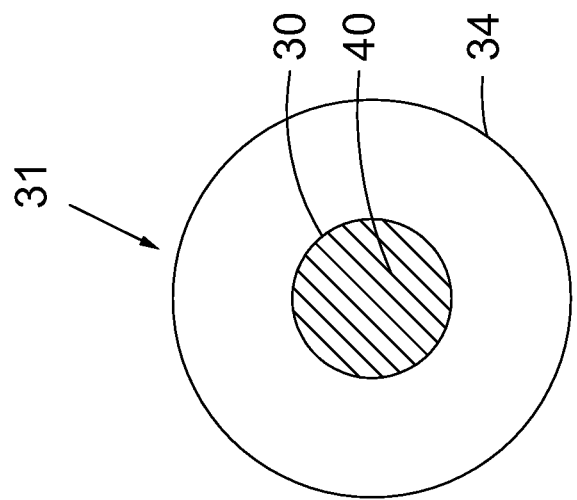
FIG. 3B is a schematic view of still another preferred embodiment of the portable cleaning article according to the art disclosed by the present invention.
Figure 3A:
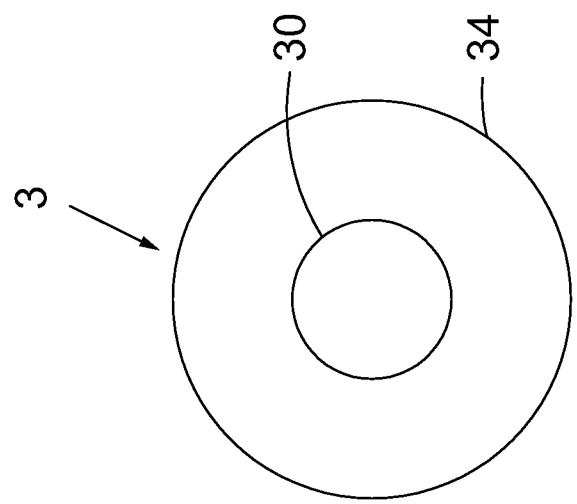
FIG. 3A is a schematic view of still another preferred embodiment of the coated capsule according to the art disclosed by the present invention.

Furthermore, FIG. 3A is a schematic view of still another preferred embodiment of coated capsule disclosed by the present invention. In FIG. 3A, the coated capsule 3 includes: a first thin-film layer 30 and a second thin-film layer 34, wherein the first thin-film layer 30 is coated by the second thin-film layer 34 to form a coated capsule 3. The molecular weight (Mw) of the first thin-film layer 30 is higher than that of the second thin-film layer 34, wherein the molecular weight (Mw) of the first thin-film layer 30 is about 4,000-40,000 and the molecular weight (Mw) of the second thin-film layer 34 is about 1,000~10,000. What is to be to explained here is that the material of the second thin-film layer 34 is partially hydrolyzed PVA. The main function groups in such partially hydrolyzed PVA are the hydroxyl groups (—OH). When the second thin-film layer 34 is in contact with water, it melts faster because there is a larger number of hydroxyl group in partially hydrolyzed PVA material to form bonds with hydrogen in water. The material for forming the first thin-film layer 30, however, is fully hydrolyzed PVA, in which there is a smaller number of hydroxyl group (—OH). Therefore, when the first thin-film layer 30 is in contact with water, the reaction of the hydroxyl group with water is slower and thus the first thin-film layer 30 also melts slower than the second thin-film layer 34 does. Thus, in the present embodiment, the molecular weight (Mw) of the second thin-film layer 34 of the coated capsule 3 is lower than that of the first thin-film layer 30 so that the first thin-film layer 30 will still be able to coat the liquid (not shown in Figure) contained within even if the second thin-film layer 34 dissolves easily when being in contact with water. Consequently, the problem that the coated capsule 3 will dissolve and break after being placed in air for long time and absorbing water vapor can be avoided.

In the following, referring to FIG. 3B, which is a schematic view of yet another embodiment of portable cleaning article disclosed by the present invention. In FIG. 3B, the portable cleaning article 31 includes: a first thin-film layer 30, a second thin-film layer 34, and liquid of certain volume 40, wherein the liquid of certain volume 40 is coated in the first thin-film layer 30, and the first thin-film layer 20 coated with oil layer 22 is further coated in the second thin-film layer 34 to form coated capsule 31 of portable cleaning article. Here, the material of the first thin-film layer 30 and the second thin-film layers 34 can be polyols such as sorbitol to increase the stability of the first thin-film layer 30 and of the second thin-film layer 34. In addition, the liquid of certain volume 40 can be a cleaning agent, water-based or oil-based, and the cleaning agent can also be a surface-active agent such as ionic surface-active agent, non-ionic surface-active agent, or amphoteric surface-active agent. In the preferred embodiment of the present invention, the liquid of certain volume 40 can be facial cleanser, body shampoo, or any kind of lotion used to protect or moisturize the skin.

Figure 4:
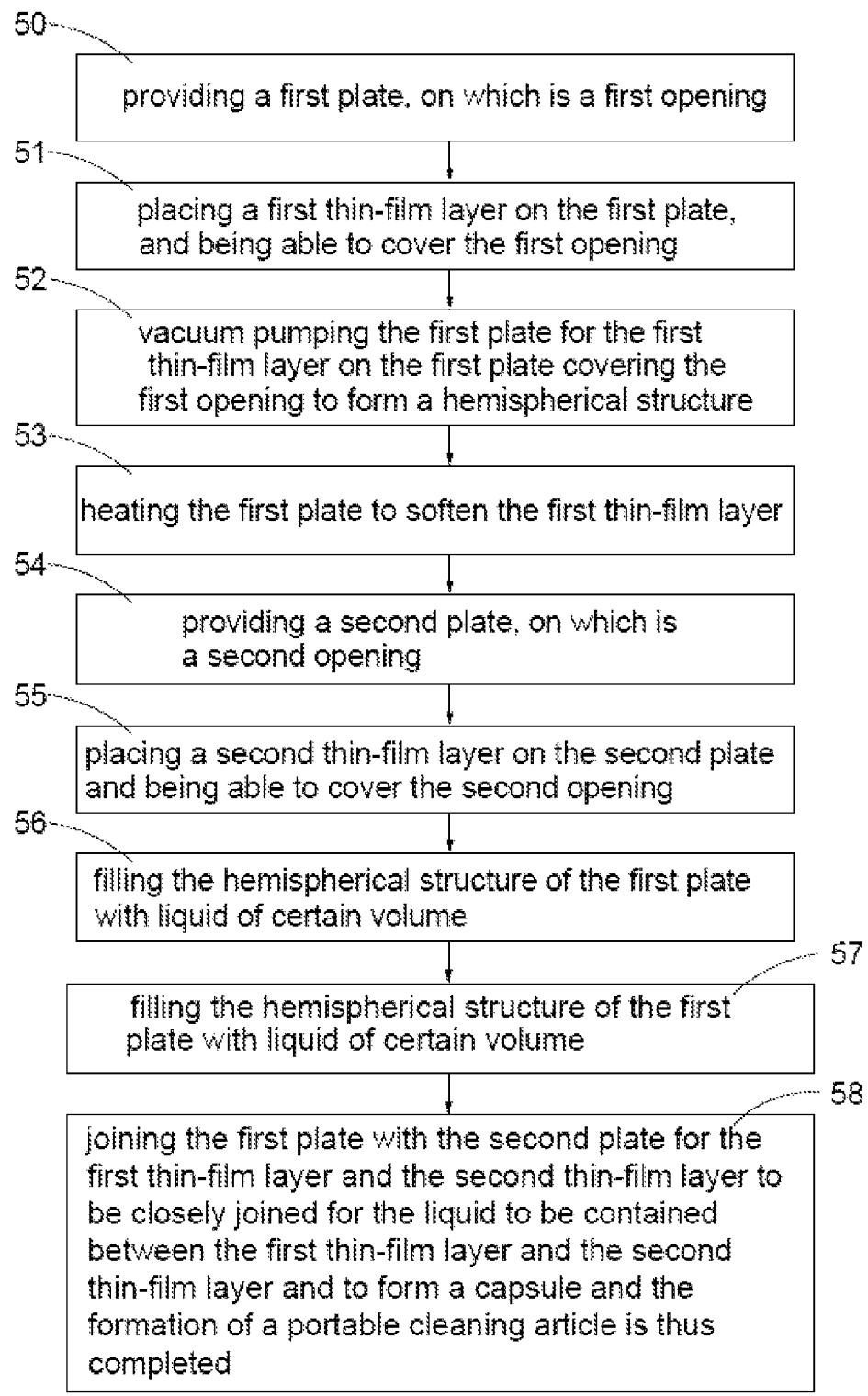
FIG. 4 is a process flow diagram of the method for forming portable cleaning article according to the art disclosed by the present invention.

Moreover, FIG. 4 is a process flow diagram manifesting the method for forming the portable cleaning article disclosed by the present invention made according to what is described above. For step 50 in FIG. 4, providing a first plate, on which is a first opening; for step 51, placing a first thin-film layer on the first plate, the square measure of the first thin-film layer being able to cover the first opening; for step 52, vacuum pumping the first plate for the first thin-film layer on the first plate covering the first opening to form a hemispherical structure; for step 53, heating the first plate to soften the first thin-film layer with heat; for step 54, providing a second plate, on which is a second opening; for step 55, placing a second thin-film layer on the second plate, the square measure of the second thin-film layer being able to cover the second opening; for step 56, heating the second plate to soften the second thin-film layer with heat; for step 57, filling the hemispherical structure of the first plate with liquid of certain volume; and for step 58, joining the first plate with the second plate for the first thin-film layer and the second thin-film layer to be closely joined for the liquid to be contained between the first thin-film layer and the second thin-film layer and to form a first capsule and the formation of a portable cleaning article is thus completed.

Figure 5:
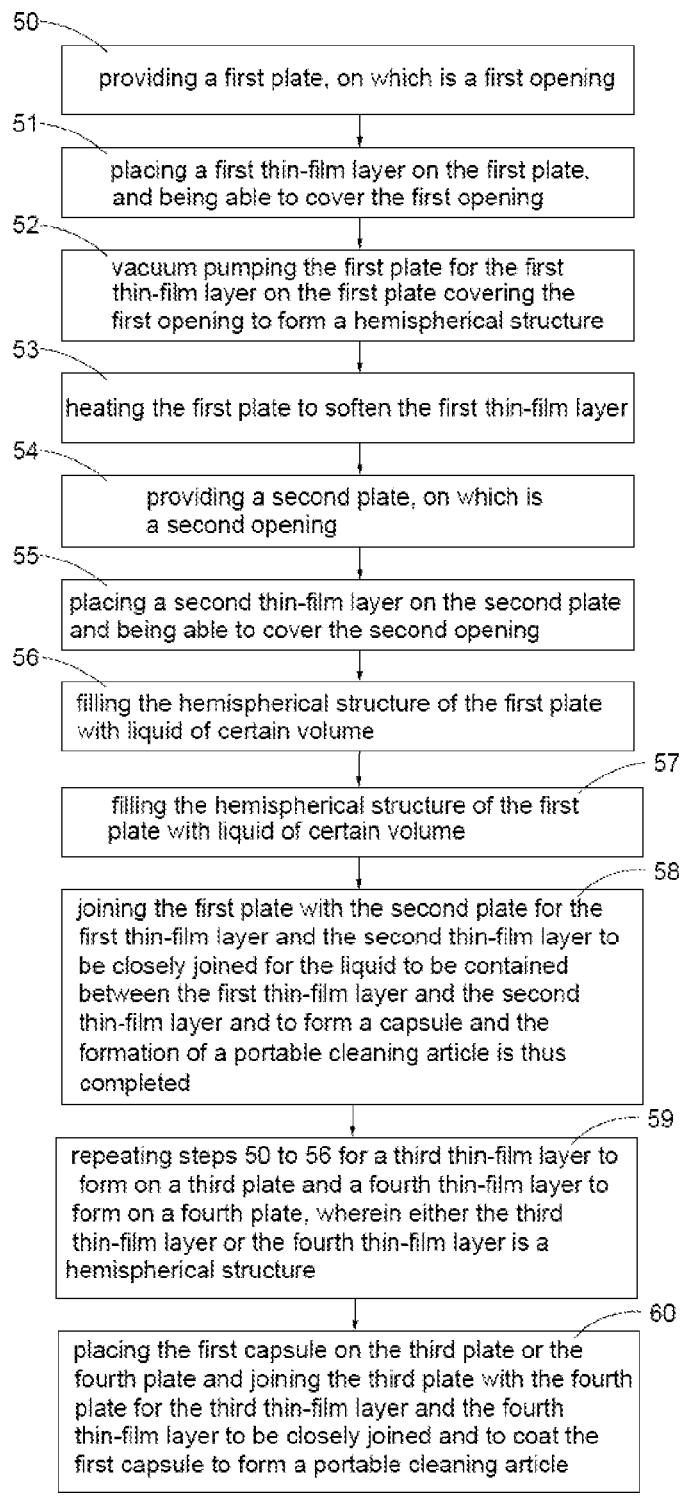
FIG. 5 is a flow diagram of another embodiment of the is method for forming portable cleaning article according to the art disclosed by the present invention.

Furthermore, FIG. 5 is a flow diagram manifesting the manufacturing method of another embodiment of the portable cleaning article disclosed by the present invention. What is to be explained here is that the steps 50 to 59 are the same as those in FIG. 4 and will not be repeated in the following. However, for step 59 in the manufacturing method demonstrated in FIG. 5, repeating steps 50 to 56 as shown in FIG. 4 for a third thin-film layer to form on a third plate and a fourth thin-film layer to form on a fourth plate, wherein either the third thin-film layer or the fourth thin-film layer is a hemispherical structure; and for step 60, placing the first capsule on the third plate or the fourth plate and joining the third plate with the fourth plate for the third thin-film layer and the fourth thin-film layer to be closely joined and to coat the first capsule to form a portable cleaning article.

What is to be made clear here is that the shape of the coated capsule as disclosed by the present invention, regardless of being in the form of single thin-film layer or of double thin-film layer, is not necessarily spherical and can also be hemispherical or elliptic.

Therefore, according to what is described above, the higher hydrophilic and lower lipophilic character of PVA (polyvinyl alcohol) can be utilized to form a thin-film to coat cleansers or lotions for protecting and moisturizing skin commonly seen in the market that completely dissolves in water and does not lead to any pollution. Moreover, the material of PVA thin-film used in the portable cleaning article disclosed by the present invention is stable to a degree and ensures that the thin-film layer in contact with the cleaning agent does not react with the cleaning agent or is result in some hard lumps as in the prior art. In addition, the portable cleaning article disclosed by the present invention not only increases the convenience for users when going on business trip or traveling by saving them the trouble to bring along so many containers and reducing the volume and weight of luggage, but also reduces pollution of the environment by serving as substitutes of containers that need to be disposed after usage.

What is claimed is:

1. A portable cleaning article, comprising a coated capsule and a cleaning agent, wherein said cleaning agent is contained in said coated capsule, the characteristic of said portable cleaning article in that:
    said coated capsule including a first thin-film layer and an oil layer coated on a surface of said first thin-film layer, wherein when said coated capsule is brought into contact with water, said coated capsule dissolves in water for said cleaning agent contained in said coated capsule to exert its cleaning function.

2. The portable cleaning article according to claim 1, wherein the molecular weight (Mw) of said first thin-film layer is about 1,000-10,000.

3. The portable cleaning article according to claim 1, further comprising a second thin-film layer that coats said oil layer and said first thin-film layer.

4. The portable cleaning article according to claim 3, wherein the molecular weight (Mw) of said second thin-film layer is the same as the molecular weight (Mw) of said first thin-film layer.

5. The portable cleaning article according to claim 3, wherein the molecular weight (Mw) of said second thin-film layer is about 4,000-40,000.

6. The portable cleaning article according to claim 1, wherein said cleaning agent is selected from the group consisting of: ionic surface-active agent, non-ionic surface-active agent, and amphoteric surface-active agent.

* * * * *